United States Patent [19]

Yamada et al.

[11] Patent Number: 4,925,977

[45] Date of Patent: May 15, 1990

[54] METHOD FOR THE PREPARATION OF NAPHTHALENE DICARBOXYLIC ACIDS

[75] Inventors: Teruaki Yamada; Yoshiji Doko; Kazuki Sugiura, all of Ibaraki, Japan

[73] Assignee: Sumikin Chemical Co., Ltd., Tokyo, Japan

[21] Appl. No.: 284,678

[22] Filed: Dec. 15, 1988

[30] Foreign Application Priority Data

Dec. 17, 1987 [JP] Japan ................................. 62-319399

[51] Int. Cl.$^5$ ...................... C07C 51/265; B01J 38/64
[52] U.S. Cl. ..................................... 562/416; 502/25; 502/152; 502/304; 502/324; 502/325; 562/414; 562/417; 562/486; 562/487; 562/488
[58] Field of Search ............... 562/416, 417, 414, 486, 562/487, 488; 502/125, 152, 304, 324, 325

[56] References Cited

U.S. PATENT DOCUMENTS

| | | | |
|---|---|---|---|
| 4,709,088 | 11/1987 | Hirose et al. | 562/414 |
| 4,764,638 | 8/1988 | Feld | 562/416 |
| 4,794,195 | 12/1988 | Hayashi et al. | 562/414 |

*Primary Examiner*—Werren B. Lone
*Assistant Examiner*—Vera C. Clarke
*Attorney, Agent, or Firm*—Burns, Doane, Swecker & Mathis

[57] ABSTRACT

An improved method for the preparation of a naphthalene dicarboxylic acid by liquid-phase catalytic oxidation of a diisopropylnaphthalene in a lower fatty acid-based solvent is disclosed wherein a catalyst system comprising bromine and the heavy metals cerium, cobalt, and manganese is used. The cerium compound used as a cerium source for the catalyst can be recovered from crystals of the naphthalene dicarboxylic acid product by dissolving the crystals in an alkali solution and separating the cerium compound as insolubles from the solution.

14 Claims, No Drawings

METHOD FOR THE PREPARATION OF NAPHTHALENE DICARBOXYLIC ACIDS

BACKGROUND OF THE INVENTION

1. Field of the Invention:

This invention relates to an improved method for the preparation of naphthalene dicarboxylic acids in which a diisopropylnaphthalene is oxidized with molecular oxygen in a solvent in the presence of an oxidation catalyst. This invention is also concerned with a method for recovering a cerium compound used as a catalytic component from a crude naphthalene dicarboxylic acid product.

Naphthalene dicarboxylic acids including 2,6- and 2,7-naphthalene dicarboxylic acid are useful as starting materials for various high-performance polymers such as polyethylene naphthalates and other polyesters, and polyamides which, in turn, are useful for manufacturing films and fibers having outstanding heat resistance and mechanical properties.

2. Prior Art:

Naphthalene dicarboxylic acids (hereinunder referred to as NDCA) such as 2,6-NDCA and 2,7-NDCA are generally prepared by oxidizing a corresponding dialkyl-naphthalene with molecular oxygen in a lower fatty acid such as acetic acid as a solvent in the presence of a catalyst system comprising bromine and at least one heavy metal selected from cobalt and manganese.

When 2,6-dimethylnaphthalene is used as a starting material for oxidation, 2,6-NDCA can be obtained with a relatively high yield. However, the synthesis of the starting 2,6-dimethylnaphthalene which may be performed by various methods including methylation of naphthalene, isomerization of other dimethyl naphthalene isomers, and disproportionation of monoethyl-naphthalene produces the desired 2,6-dimethyl isomer with a very low yield and the product always contains considerble amounts of other isomer. There are ten isomers of dimethylnaphthalene having similar physical properties, and it is rather difficult to separate the 2,6-isomer from a mixture of different isomers. Therefore, the preparation of 2,6-NDCA from 2,6-dimethylnaphthalene is not economical.

On the other hand, diisopropylnaphthalenes (hereinbelow referred to as DIPN) can be easily synthesized, and it is relatively easy to separate the individual isomers thereof, e.g., the 2,6-isomer and the 2,7-isomer from a mixture of various isomers. However, the use of DIPN as a starting material to prepare NDCA by oxidation has the disadvantage that the yield of the oxidation product, NDCA, is much lower than when a dimethylnaphthalene is employed as a starting material.

There have been many proposals of methods for increasing the yield when preparing 2,6-NDCA from 2,6-DIPN by oxidation with molecular oxygen in the presence of a catalyst system comprising bromine and at least one heavy metal selected from cobalt and manganese.

These include a method in which at least 0.2 moles of the heavy metal are used for each mole of 2,6-DIPN or an intermediate thereof (Japanese Published Unexamined patent application No. 60-89445); a method in which the heavy metal is present in an amount of at least 1% based on the weight of the solvent (Japanese Published Unexamined patent application No. 60-89446); a method in which the catalyst system further contains an alkali metal (Japanese Published Unexamined patent application No. 61-246143); and a method in which bromine is present in an amount of 0.1%–10% based on the weight of the solvent (Japanese Published Unexamined patent application No. 61-246144).

It has also been proposed that a catalyst system comprising bromine and the heavy metals cobalt and cerium or nickel be used in order to increase the yield of 2,6-NDCA (Japanese Published Unexamined patent applications Nos. 62-212344 and 62-212343).

It is also important in the commercial production of NDCA by the above-mentioned catalytic oxidation to recover the expensive heavy metal catalytic components for reuse in order to reduce production costs.

With respect to a similar reaction system in which terephthalic acid is prepared by liquid-phase oxidation of p-xylene in the presence of a Br-Co-Mn catalyst system, it has been proposed that after the resulting terephthalic acid is collected by filtration, the cobalt and manganese be recovered as carbonates from the filtrate following evaporation of the solvent (Japanese patent Publication No. 46-14399 and Japanese Published Unexamined application No. 47-34088). Japanese Published Unexamined application No. 49-106986 discloses that the recovered cobalt and manganese components can be subjected to oxidation with molecular oxygen to remove the undesirable by-products deposited thereon and to enhance the activity of the recovered catalytic components.

With respect to the catalytic oxidation of 2,6-DIPN into 2,6-NDCA, Japanese Published Unexamined patent application No. 62-212345 discloses a process in which the reaction mixture is withdrawn from a reactor, crude 2,6-NDCA crystals precipitated are separated, and then washed with an aqueous solution of a mineral acid to dissolve and remove the heavy metal catalytic components (Co and Mn). The crystals are then subjected to salting-out with an alkali solution to precipitate dialkali salt of 2,6-NDCA, while the acidic washings are treated with an alkali carbonate to recover the heavy metal catalytic components as carbonates.

However, the recovery of other metallic components such as a cerium compound used in the catalyst from the reaction mixture of a catalytic oxidation of DIPN is not taught in the prior art.

SUMMARY OF THE INVENTION

It is an object of this invention to provide an improved method for the prepartion of NDCA with a high yield from the corresponding DIPN by a liquid-phase catalytic oxidation.

Another object of this invention is to provide a method for the recovery of a cerium compound from the NDCA product obtained by the catalytic oxidation.

We have made many investigations of the liquid-phase catalytic oxidation of DIPN into NDCA with molecular oxygen, and found that the above-described first object can be attained by using a catalyst which comprises bromine and the three heavy metals cerium, cobalt, and manganese as catalytically active components. We also have found that the cerium compounds used as a cerium source in the catalyst is entrained by a crude NDCA product and it can be separated and recovered as insolubles by dissolving the NDCA crystals in an alkali solution Thus, in one aspect, the present invention provides a method for the preparation of an NDCA by catalytic oxidation of the corresponding DIPN with molecular oxygen in a solvent containing a lower fatty acid, wherein the oxidation is carried out in the presence of an oxidation catalyst system comprising bromine and the heavy metals cerium, cobalt, and manganese.

In another aspect, the present invention provides a method for the recovery of a cerium compound from a mixture of NDCA and the cerium compound, which comprises adding an aqueous alkali solution to the mixture in an amount sufficient to dissolve the NDCA as its dialkali metal salt, and separating and recovering the cerium compound as insolubles from the solution.

DESCRIPTION OF THE PREFERRED EMBODIMENTS

In the preparation method of NDCA according to the present invention, any isomer of DIPN can be used as a starting material In view of the usefulness of the NDCA product, it is preferred to use the 2,6-isomer, the 2,7-isomer, or a mixture of these isomers. An oxidation intermediate formed in the catalytic oxidation of DIPN in which at least one of the isopropyl groups is replaced by the group of the formula

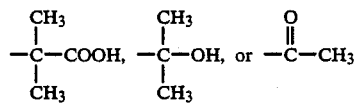

may be used as a starting material.

The solvent which is used in the present invention can be a lower fatty acid or a mixture of a lower fatty acid and one or more of other solvents. Examples of useful lower fatty acids are $C_1$–$C_4$ aliphatic monocarboxylic acid such as acetic acid, propionic acid, and butyric acid, and acetic acid is most preferable. When the lower fatty acid is mixed with another solvent, it is preferable to use a solvent which has a relatively high stability for oxidation. Examples of such a solvent are chlorobenzene and bromobenzene. In the case of a mixed solvent, it is preferable that the lower fatty acid comprise at least 30% by weight of the solvent.

The oxidation catalyst system used in the present invention comprises bromine and the heavy metals cerium, cobalt, and manganese as active components. The compounds used to form the catalyst system are preferably soluble in the above-described solvent. Suitable compounds for use as sources of the heavy metals cerium, cobalt, and manganese include acetates and other fatty acid salts, halides, oxides, hydroxides, and carbonates of these metals. Particularly preferable metallic compounds for the catalyst are acetates and bromides of cerium, cobalt, and manganese. Useful bromine compounds as a bromine source include molecular bromine, hydrogen bromide, alkyl bromides, ammonium bromide, and various metal bromides. Particularly preferred are potassium bromide, sodium bromide, and the like It is also possible to add an alkali metal compound such as potassium acetate or sodium acetate, or a ketone such as methyl ethyl ketone or acetaldehyde to the reaction system in order to promote the catalytic activity.

The atomic ratio of the heavy metals in the catalyst system preferably satisfies the inequality $$0.01 \leq Ce/(Co + Mn) \leq 10, \text{ and more preferably}$$

-continued $$0.1 \leq Ce/(Co + Mn) \leq 1.5.$$

If the amount of cerium is such that the atomic ratio is outside of these ranges, the yield of NDCA tends to fall.

The total amount of heavy metals is at least 0.1 gram-atoms and at most 10 gram-atoms and preferably at least 0.2 and at most 2.0 gram-atoms per mole of the starting DIPN. If the amount is less than 0.1 gram-atoms or greater than 10 gram-atoms per mole of DIPN, the yield of NDCA will decrease.

The concentration of the catalytic elements (the heavy metals and bromine) is at least 0.5% by weight and preferably at least 1.0% by weight of each of the total amount of heavy metals and the amount of bromine based on the weight of the solvent.

Air can be conveniently used as a gas containing molecular oxygen. Alternatively, air or oxygen which has been diluted with an inert gas can be employed. Pure oxygen gas may also be used.

When air is employed as a molecular oxygen-containing gas, the pressure during reaction is 10–60 $kg/cm^2$ and preferably 23–45 $kg/cm^2$.

The reaction temperature is 150°–210° C. and preferably 180°–200° C.

The reaction may be carried out batch-wise or continuously. In order to minimize undesirable side-reactions, it is preferable to carry out the reaction by feeding the starting DIPN very slowly over an extended time under superatmospheric pressure with the molecular oxygen-containing gas into a solution of the catalyst dissolved in the solvent which has been placed in a reactor. After the addition of DIPN is completed, the reaction mixture may be subjected to post-oxidation by introducing only the oxygen-containing gas into the reactor in order to convert unreacted DIPN and oxidation intermediates into NDCA product and decompose undesirable by-products.

When cerium is present in the catalyst system in combination with cobalt and manganese according to the present invention, compared to the conventional catalyst system in which the heavy metals present are cobalt and/or manganese, there is the advantage that the synergistic effect of the three heavy metals Co, Mn, and Ce produces a high yield of NDCA.

Furthermore, when the conventional catalyst system is used, a pipe for introducing an oxygen-containing gas may become blocked, and the reaction product tends to adhere to the inner wall of the reactor. These problems must be eliminated in the commercial production of NDCA. By the addition of a cerium compound according to the present invention, it has been found that unexpected results are obtained that there is almost no blocking of the pipe for introducing an oxygen-containing gas or adhesion of the reaction product to the inner wall of the reactor. When cerium is present in the catalyst system, the crystals of the NDCA formed by the catalytic oxidation are extremely fine, and it is believed that this contributes to the prevention of blocking and adhesion.

By using a cerium-containing catalyst system according to the present invention, the maximum amount of water which is permitted to be present in the reaction system without causing a substantial decrease in the yield of NDCA is higher than for the conventional catalyst system comprising bromine and cobalt and/or manganese. As a result, the combustion rate of the solvent such as acetic acid can be minimized by maintaining a relatively high concentration of water in the reaction mixture, and the loss of the solvent can be decreased thereby.

Since the NDCA product has a low solubility in the lower fatty acid-based solvent, crude NDCA crystals can be readily collected from the reaction mixture upon cooling by a suitable means such as filtration or centrifugal separation. It is advantageous to recover the heavy metal compounds used as catalytic components from the reaction mixture for reuse.

We tried to recover the heavy metals cerium, cobalt, and manganese from the reaction medium remaining after the crude NDCA crystals had been separated from the reaction mixture. Specifically, the reaction medium was concentrated to recover the lower fatty acid used as the solvent, and the residue was treated in the conventional manner so as to recover the metallic components. As a result, almost all of the cobalt and manganese components used in the catalyst system could be recovered from the residue, while the cerium component recovered from the residue was only about 0.1 mole % relative to the amount initially used for the reaction.

It was found that the above low recovery rate of the cerium component was due to the fact that most of the cerium component was entrained by the crude NDCA crystals rather than being contained in the reaction medium. Thus, the determination of the cerium content of the crude NDCA crystals separated from the reaction mixture indicated that the crystals contained almost all the cerium components initially used in the reaction. This is surprising since the other heavy metallic components (cobalt and manganese) still remained dissolved in the solvent and could be recovered from the reaction medium.

Next, in order to recover cerium from the crude NDCA crystals, we tried various separation methods using organic solvents capable of dissolving NDCA, or mineral acid solutions such as sulfuric acid and hydrochloric acid solutions for dissolving cerium, but none of them could separate cerium with high efficiency. For example, N,N-dimethylacetamide, N,N-dimethylformamide, dimethylsulfoxide, and similar solvents are known to be capable of dissolving NDCA, but the solubility of NDCA in these solvents is not so high and these solvents are too expensive to be used in a commercial process. None of the solvents or acidic solutions which were tested could dissolve cerium without dissolving NDCA.

Finally, it has been found that NDCA can be dissolved in an aqueous alkali solution in the form of its dialkali metal salt, while the cerium remains undissolved in the solution and can be recovered as insolubles. The use of an aqueous alkali solution makes it possible to separate a cerium compound from NDCA with high efficiency and to recover substantially all the cerium present in the crude NDCA crystals.

According to one embodiment of the present invention, the crude NDCA crystals which contain cerium compounds used as a catalytic component are treated with an aqueous alkali solution in an amount sufficient to dissolve the NDCA as its dialkali metal salts. Useful alkali solutions include aqueous solutions of sodium hydroxide, potassium hydroxide, sodium carbonate, potassium carbonate, sodium hydrogen carbonate, and potassium hydrogen carbonate.

It is preferred to use an alkali solution having a concentration in the range of 0.5-15% by weight. The alkali solution is preferably used in such an amount that provides from 2 to 10 equivalents of the alkali metal, more preferably from 2.5 to 5 equivalents of the alkali metal per mole of NDCA. The mixture of the NDCA crystals and the alkali solution is stirred for a period sufficient to dissolve all the NDCA crystals as dialkali metal salts. In order to reduce the stirring period, the mixture may be heated at a temperature up to the reflux temperature.

After the mixture is stirred sufficiently, the NDCA is completely dissolved in the alkali solution, but the cerium compound still remains undissolved and can be separated by a conventional solid-liquid separation device such as a centrifuge or filter press to recover substantially all the cerium component initially used for the reaction. The cerium compound thus recovered may be recycled to the reaction as a catalytic component and it can exert the same degree of catalytic activity as the fresh cerium compound.

After separation of the cerium-containing insolubles, the remaining NDCA dialkali metal salt in solution may be converted into free acid by neutralization.

The other heavy metals cobalt and manganese can be recovered from the reaction medium obtained after separating the crude NDCA crystals by a conventional method. A suitable method for recovering cobalt and manganese from the reaction medium involves concentrating the reaction medium to recover the solvent and treating the residue with a suitable carbonate salt such as an alkali metal carbonate or an alkali metal hydrogen carbonate to precipitate and recover these metals as carbonates. The recovered cobalt and manganese carbonate can also be recycled to the reaction as catalytic components.

Thus, according to the present method, all the heavy metal catalytic components can be recovered without substantial loss and can be reused. This diminishes the cost of the catalyst and is advantageous in the commercial production of NDCA.

The present invention will now be described in further detail by the following examples. It should be understood that the examples are intended merely to illustrate the invention, and the present invention should not be construed to be restricted by the examples.

EXAMPLE 1

A 0.5-liter titanium autoclave was charged with 4.98 g of cobalt acetate tetrahydrate, 4.89 g of manganese acetate tetrahydrate, 6.71 g of cerium acetate monohydrate, 7.14 g of potassium bromide, and 5.91 g of potassium acetate as catalytic components and 230 g of acetic acid as a solvent. The contents of the autoclave were heated to 200° C. with stirring, and excess air was blown into the autoclave so as to maintain a reaction pressure at 30 kg/cm$^2$. While maintaining the temperature at 200° C. and the pressure at 30 kg/cm$^2$ under stirring and air blowing, 62.70 g of 2,6-DIPN were introduced over a period of 4 hours, after which post-oxidation was performed for 1 hour by introducing only air. After the completion of the reaction, precipitated crystals were collected as a reaction product by filtration of the reaction mixture and were washed with hot water to give crude 2,6-NDCA as yellowish-white crystals. The yield of 2,6-NDCA was 94.5 mole % relative to 2,6-DIPN.

During the reaction, no adhesion of the reaction product to a pipe for blowing air or to the inner wall of the autoclave was observed.

In this example, the total amount of heavy metals in the catalyst system was 0.203 gram-atoms per mole of 2,6-DIPN. The total amount of the heavy metal compounds used was 2.21% by weight as metallic elements, and the amount of the bromine compound used was 2.07% by weight as Br, both based on the weight of the solvent. The atomic ratio Ce/(Co+Mn) was 1.23.

EXAMPLE 2

Catalytic oxidation of DIPN into NDCA was performed in the same manner as described in Example 1 except that 2,7-DIPN was used as the starting material in place of 2,6-DIPN. Yellowish-white crystals were recovered as a reaction product. The yield of 2,7-NDCA was 94.3 mole %.

In this reaction, no adhesion whatsoever of the reaction product to the pipe for blowing air or to the inner wall of the autoclave was observed.

Comparative Example 1

Using 2.48 g of cobalt acetate tetrahydrate, 2.44 g of manganese acetate tetrahydrate, 83.30 g of cerium acetate monohydrate, 16.20 g of potassium bromide, and 13.37 g of potassium acetate as catalytic components, catalytic oxidation of 2,6-DIPN was performed in the same manner as described in Example 1. Blackish-brown crystals were recovered as a reaction product. The yield of 2,6-NDCA was 36.0 mole %. In this example, the atomic ratio Ce/(Co+Mn) was 12.5.

Comparative Example 2

Using 7.48 g of cobalt acetate tetrahydrate, 7.37 g of manganese acetate tetrahydrate, 7.14 g of potassium bromide, and 5.91 g of potassium acetate as catalytic components, catalytic oxidation of 2,6-DIPN was performed in the same manner as described in Example 1. A reaction product in the form of yellowish-white crystals was recovered. The yield of 2,6-NDCA was 87.2 mole %.

Adhesion of the reaction product to the pipe for blowing air and to the inner wall of the autoclave was observed in the reaction.

The total amount of heavy metals used in the reaction was 0.203 gram-atoms per mole of 2,6-DIPN or 2.21% by weight based on the weight of the solvent, and the amount of bromine was 2.07% by weight based on the solvent

Comparative Example 3

Catalytic oxidation of 2,6-DIPN was performed in the same manner as described in Example 1 except that the reaction temperature was 220° C. rather than 200° C. Black crystals were recovered as a reaction product. The yield of 2,6-NDCA was 50.2 mole %.

The total amount of heavy metals used in the reaction was 0.203 gram-atoms per mole of 2,6-DIPN or 2.21% by weight based on the weight of the solvent, and the amount of bromine was 2.07% by weight based on the solvent.

Comparative Example 4

Using 1.66 g of cobalt acetate tetrahydrate, 1.63 g of manganese acetate tetrahydrate, 2.24 g of cerium acetate monohydrate, 2.47 g of potassium bromide, and 1.97 g of potassium acetate as catalytic components, catalytic oxidation of 2,6-DIPN was carried out in the same way as described in Example 1. Blackish-brown crystals were recovered as a reaction product. The yield of 2,6-NDCA was 42.8 mole %.

The total amount of heavy metals used in the reaction was 0.068 gram-atoms per mole of 2,6-DIPN or 0.74% by weight based on the weight of the solvent, and the amount of bromine was 0.72% by weight based on the solvent.

Comparative Example 5

The procedure described in Example 1 was repeated under the same conditions as for Example 1 except that 0.83 g of cobalt acetate tetrahydrate, 0.82 g of manganese acetate tetrahydrate, 1.12 g of cerium acetate monohydrate, 2.47 g of potassium bromide, and 1.97 g of potassium acetate were used as catalytic components, and that 10.45 g of 2,6-DIPN were introduced over a period of 40 minutes. Light yellow crystals were recovered as a reaction product. The yield of 2,6-NDCA was 44.3 mole %.

The total amount of heavy metals used in the reaction was 0.203 gram-atoms per mole of 2,6-DIPN or 0.37% by weight based on the weight of the solvent, and the amount of bromine was 0.72% by weight based on the solvent.

Comparative Example 6

Using 4.98 g of cobalt acetate tetrahydrate, 4.89 g of manganese acetate tetrahydrate, 6.71 g of cerium acetate monohydrate, 1.43 g of potassium bromide, and 1.18 g of potassium acetate as catalytic components, catalytic oxidation of 2,6-DIPN was performed in the same manner as described in Example 1. Yellowish-white crystals were recovered as a reaction product. The yield of 2,6-NDCA was 53.1 mole %.

The total amount of heavy metals used in the reaction was 0.203 gram-atoms per mole of 2,6-DIPN or 2.21% by weight based on the weight of the solvent, and the amount of bromine was 0.41% by weight based on the solvent.

Comparative Example 7

Using 7.48 g of cobalt acetate tetrahydrate, 10.08 g of cerium acetate monohydrate, 7.14 g of potassium bromide, and 5.91 g of potassium acetate as catalytic components, catalytic oxidation of 2,6-DIPN was performed in the same manner as described in Example 1. Pale yellow crystals were recovered as a reaction product. The yield of 2,6-NDCA was 75.1 mole %.

The total amount of heavy metals used in the reaction was 0.203 gram-atoms per mole of 2,6-DIPN or 2.21% by weight based on the weight of the solvent, and the amount of bromine was 2.07% by weight based on the solvent.

In Comparative Examples 1 and 3-7, there was almost no adhesion of reaction product to the pipe for blowing air or to the inner walls of the autoclave.

EXAMPLE 3

The procedure described in Example 1 was repeated in exactly the same manner. After the reaction mixture was subjected to post oxidation for one hour and then cooled to room temperature, crude 2,6-NDCA crystals were collected by filtration. The crystals were then washed with hot water to remove the cobalt and manganese compounds deposited thereon, and dried in vacuo. The yield of 2,6-NDCA was 94.1 mole %.

All the crystals of 2,6-NDCA recovered in the above were added to 600 g of a 10% aqueous sodium hydroxide solution and dissolved therein with stirring. The resulting solution was heated at reflux for one hour. The remaining insolubles (hereinafter referred to as alkali insolubles) were then separated by filtration from the solution, and washed with water. The heavy metal content of the separated alkali insolubles was determined by plasma emission analysis. They were found to contain 99.8% of cerium, 0.2% of cobalt, and 0.6% of manganese based on the weight of each metal initially used in the reaction. Thus, in spite of the fact that all the heavy metals were added as acetates, only the cerium acetate was entrained by the NDCA product, while cobalt and manganese acetates still remained in the reaction medium separated from the product.

The alkali insolubles obtained in the above manner were used in place of the cerium acetate, and they were added to the same autoclave as used above together with cobalt acetate, manganese acetate, potassium bromide, potassium acetate, and acetic acid all of which were used in the same amounts as employed in the first run, i.e., the same as in Example 1. A second run was performed under the same reaction conditions as in the first run by introducing 2,6-DIPN over 4 hours followed by post-oxidation for one hour. The resulting 2,6-NDCA crystals were collected and treated in the same manner as described above. In the second run, the yield of 2,6-NDCA was 93.8%, and 99.6% of cerium based on the weight of cerium used in the first run was recovered as the alkali insolubles. The alkali insolubles recovered in the second run contained 0.3% of cobalt and 0.5% of manganese based on the weight of each metal used in the first run.

The above procedure was repeated in the third and following runs, and a total of ten runs of catalytic oxidation of 2,6-DIPN were performed with the recovered alkali insolubles being recycled as a cerium component. The yield of 2,6-NDCA and the analysis of the recovered alkali insolubles for heavy metals were determined in the fifth and the tenth (final) runs. The results are shown in Table 1.

TABLE 1

| Run No. | 1 | 2 | 5 | 10 |
|---|---|---|---|---|
| % Yield of 2,6-NDCA | 94.1 | 93.8 | 92.3 | 92.8 |
| % Recovery of Ce | 99.8 | 99.6 | 99.5 | 99.5 |
| % Co in alkali insolubles | 0.2 | 0.3 | 0.2 | 0.3 |
| % Mn in alkali insolubles | 0.6 | 0.5 | 0.4 | 0.5 |

As can be seen from Table 1, substantially all the cerium could be recovered and recycled to the reaction without adversely affecting the results of the reaction including the yield of 2,6-NDCA product.

EXAMPLE 4

The procedure described in Example 3 was repeated except that the sodium hydroxide solution used for dissolving the collected NDCA crystals and recovering cerium-containing alkali insolubles was replaced by an aqueous sodium carbonate solution having the same concentration (10% by weight). By using the recovered alkali insolubles as the cerium source, a total of ten runs of the reaction were carried out in the same manner as described in Example 3. The results are summarized in Table 2.

TABLE 2

| Run No. | 1 | 2 | 5 | 10 |
|---|---|---|---|---|
| % Yield of 2,6-NDCA | 93.8 | 92.7 | 93.1 | 92.4 |
| % Recovery of Ce | 99.7 | 99.5 | 99.4 | 99.4 |
| % Co in alkali insolubles | 0.3 | 0.4 | 0.5 | 0.4 |
| % Mn in alkali insolubles | 0.5 | 0.6 | 0.6 | 0.5 |

As can be seen from Table 2, substantially all the cerium could be recovered and recycled to the reaction.

EXAMPLE 5

The procedure described in Example 3 was repeated except that the sodium hydroxide solution used for treating the collected NDCA crystals was replaced by an aqueous potassium hydroxide solution having the same concentration (10% by weight). By using the recovered alkali insolubles as the cerium source, a total of ten runs of the reaction were carried out in the same manner as described in Example 3. The results are summarized in Table 3.

TABLE 3

| Run No. | 1 | 2 | 5 | 10 |
|---|---|---|---|---|
| % Yield of 2,6-NDCA | 94.2 | 94.0 | 93.5 | 93.6 |
| % Recovery of Ce | 99.6 | 99.6 | 99.5 | 99.4 |
| % Co in alkali insolubles | 0.2 | 0.2 | 0.4 | 0.2 |
| % Mn in alkali insolubles | 0.5 | 0.6 | 0.5 | 0.5 |

As can be seen from Table 3, substantially all the cerium could be recovered and recycled to the reaction while maintaining a high yield of the product.

Although the present invention has been described with respect to preferred embodiments, it should be understood that variations and modifications may be made without departing from the scope of the invention as defined by the following claims.

We claim:

1. In a method for the preparation of a naphthalenedicarboxylic acid by catalytic oxidation of a diisopropylnaphthalene with molecular oxygen in a solvent containing a lower fatty acid in the presence of an oxidation catalyst system comprising a bromine compound and a compound of each of the heavy metals, cerium, cobalt, and manganese, the improvement wherein the oxidation catalyst further comprises a potassium compound.

2. A method as claimed in claim 1 wherein the diisopropylnaphthalene is 2,6- or 2,7-diisopropylnaphthalene or a mixture thereof.

3. A method as claimed in claim 1 wherein the atomic ratio of the heavy metals present in the catalyst system satisfies the following inequality:

$$0.1 \leq Ce/(Co+Mn) \leq 10.$$

4. A method as claimed in claim 3 wherein the atomic ratio of the heavy metals present in the catalyst system satisfies the following inequality:

$$0.1 \leq Ce/(Co+Mn) \leq 1.5.$$

5. A method as claimed in claim 1 wherein the catalytic oxidation reaction is carried out at a temperature of from 150° to 210° C.

6. A method as claimed in claim 1 wherein the total amount of heavy metals present in the catalyst system is in the range of 0.1 to 10 gram-atoms per mole of diisopropylnaphthalene.

7. A method as claimed in claim 6 wherein the total amount of heavy metals is in the range of from 0.2 to 2.0 gram-atoms per mole of diisopropylnaphthalene.

8. A method as claimed in claim 1 wherein each of the amount of bromine and the total amount of heavy metals present in the catalyst system is at least 0.5% by weight based on the weight of the solvent.

9. A method as claimed in claim 8 wherein each of the amount of bromine and the total amount of heavy metals present in the catalyst system is at least 1.0% by weight based on the weight of the solvent.

10. A method as claimed in claim 1 which further includes separating crystals of naphthalene dicarboxylic acid product from the reaction mixture and recovering the cerium compound used as a cerium source from the crystals by dissolving the crystals in an aqueous alkali solution and separating the cerium compound from the solution as insolubles.

11. A method as claimed in claim 10 wherein the cerium compound is cerium acetate or cerium bromide.

12. A method as claimed in claim 10 wherein the alkali solution is an aqueous solution of sodium hydroxide, potassium hydroxide, sodium carbonate, potassium carbonate, sodium hydrogen carbonate, or potassium hydrogen carbonate.

13. A method as claimed in claim 10 which further includes recovering the cobalt and manganese compounds used as cobalt and manganese sources, respectively, from the reaction medium remaining after separation of crystals of naphthalene dicarboxylic acid product.

14. A method for the recovery of a cerium compound from a mixture of a naphthalene dicarboxylic acid and the cerium compound, which comprises adding an aqueous solution to the mixture in an amount sufficient to dissolve the naphthalene dicarboxylic acid as its dialkali metal salt, and separating and recovering the cerium compound as insolubles from the solution.

* * * * *